(12) United States Patent
Andersen

(10) Patent No.: US 6,511,474 B1
(45) Date of Patent: Jan. 28, 2003

(54) BOLUS FOR NON-OCCLUDING HIGH FLOW ENTERAL FEEDING TUBE

(75) Inventor: Erik Andersen, Gurnee, IL (US)

(73) Assignee: Corpak, Inc., Wheeling, IL (US)

( * ) Notice: Subject to any disclaimer, the term of this patent is extended or adjusted under 35 U.S.C. 154(b) by 172 days.

(21) Appl. No.: 09/614,360

(22) Filed: Jul. 12, 2000

(51) Int. Cl.$^7$ .................................................. A61J 15/00

(52) U.S. Cl. ........................ 604/910; 604/264; 604/268; 604/270; 604/516

(58) Field of Search ................................ 604/264, 268, 604/270, 516, 910; 128/270.14

(56) References Cited

U.S. PATENT DOCUMENTS

| | | | |
|---|---|---|---|
| 4,496,347 A | * | 1/1985 | MacLean et al. ............. 600/434 |
| 4,594,074 A | | 6/1986 | Andersen et al. ............. 604/270 |
| 4,769,014 A | * | 9/1988 | Russo ........................... 604/270 |
| 4,781,704 A | * | 11/1988 | Potter ........................... 604/105 |
| 4,863,424 A | * | 9/1989 | Blake et al. .................. 604/103 |
| 5,451,216 A | | 9/1995 | Quinn ........................... 604/270 |
| 5,571,093 A | | 11/1996 | Cruz et al. ................... 604/270 |
| 5,599,322 A | | 2/1997 | Quinn ........................... 604/270 |
| 5,665,064 A | * | 9/1997 | Bodicky et al. ............. 600/156 |
| 5,810,787 A | | 9/1998 | Quinn ........................... 604/270 |
| 5,910,128 A | * | 6/1999 | Quinn ........................... 604/93 |
| 6,066,112 A | * | 5/2000 | Quinn ........................... 604/93 |
| 6,358,197 B1 | * | 3/2002 | Silverman et al. ........... 600/29 |

OTHER PUBLICATIONS

"Silk Over–The–Wire Jejunostomy Tube" brochure, copyright 1993.

"Corscope Endoscopically Placed Feeding Tube" brochure, copyright 1992.

* cited by examiner

Primary Examiner—Thomas Denion
Assistant Examiner—Ching Chang
(74) Attorney, Agent, or Firm—Bell, Boyd & Lloyd, LLC

(57) ABSTRACT

The present invention is a bolus for an enteral feeding tube, or catheter, that is capable of being used in an over-the-wire intubation procedure as well as other intubation procedures. The bolus has a generally tubular body defining a sidewall, a proximal end tube opening capable of being connected to a distal end of the enteral feeding tube, and a generally rounded terminal end having a flattened tip. The bolus includes a fluid opening within the sidewall of the bolus between the proximal end opening and the terminal end of the bolus. An interior surface of the sidewall opposite the fluid opening is curved and slopes upwardly toward a distal end of the fluid opening. The curved interior surface and the fluid opening configuration allows for fluid flow that approximates the fluid flow rate characteristics of an open-ended tube. The fluid opening is biased toward the terminal end of the bolus thereby defining an elongated collar portion adjacent the proximal end tube opening of the bolus. The terminal end of the bolus has an aperture therethrough that forms a stylet passage in communication with the fluid opening. The stylet passage is sized to allow a stylet to pass therethrough when the tube is used in an over-the-wire intubation procedure.

34 Claims, 3 Drawing Sheets

BOLUS FOR NON-OCCLUDING HIGH FLOW ENTERAL FEEDING TUBE

TECHNICAL FIELD

The present invention generally relates to the irrigation, administration and aspiration of fluids to and from body cavities such as the gastrointestinal tract through a catheter and, in particular, to an enteral feeding tube having a non-collapsible bolus containing a fluid opening disposed at a distal end of the tube.

BACKGROUND OF THE INVENTION

Enteral nutrition is a form of hyperalimentation and metabolic support in which nutrient formulas or medicaments are delivered directly to the gastrointestinal tract. Fluid administration and aspiration is accomplished through use of a nasogastrointestinal tube generally referred to as an enteral feeding tube, as shown in FIG. 1. Enteral feeding is frequently utilized where adequate nutritional intake cannot be achieved through oral alimentation because of poor appetite, chronic nausea, general apathy, sedation or other symptoms or characteristics associated with serious disease. By delivering appropriate nutrient fluids directly to the gastrointestinal tract through an enteral feeding tube, nutritional and metabolic support of the patient is achieved without risk of sepsis or metabolic derangement, which may occur in intraveneous hyperalimentation. Because of increasing emphasis on out-patient care, enteral nutrition has been recognized as a desirable method of hyperalimentation as it requires only oral intubation of the feeding tube rather than manipulation of sterile cannulae or other means of interconnection with surgically implanted subclavian catheters as used in parenteral hyperalimentation.

Prior art feeding tubes, or catheters, typically include a rigid tip, or bolus, that includes a fluid outlet that promotes fluid flow. The fluid outlet is typically provided through a sidewall of the bolus to guard against occlusion with mucous, gastrointestinal debris or coagulated feeding material. The bolus is also more rigid than the enteral tube so that the tube can be easily guided during the intubation procedure. The enteral tube may also be provided with a wire stylet within the tube to provide more rigidity to the tube during intubation. The stylet can then be removed when the tube is inserted to the desired position within the gastrointestinal tract. Inadvertent exiting of the stylet during intubation is reduced by positioning the fluid outlet within the sidewall of the bolus.

In some situations, the enteral tube is introduced into the gastrointestinal tract in an over-the-wire intubation procedure. This procedure requires a bolus having an open ended tip. A wire stylet, or guide wire, extends through the enteral tube and out the open end of the bolus tip. The guide wire is used to guide the enteral tube and bolus to a location that may be more difficult to reach. The guide wire provides more control over the tube and bolus for placement in these locations. For example, the guide wire may be used to guide the bolus and enteral tube through the stomach and into the jejunum or duodenum. The guide wire, which is relatively stiff compared to the enteral tube, is inserted ahead of the bolus to a desired position. The enteral tube is then slipped over the wire and advanced to the desired position. When the enteral tube is properly placed, the wire is removed.

One disadvantage in the prior art is that an over-the-wire intubation procedure typicall requires a bolus having a different design than those used in other procedures. Prior art boluses for use in an over-the-wire procedure are typically open-ended tubes that do not incorporate a rounded tip. On the other hand, boluses used in other types of intubation procedures typically have a rounded or bullet-shaped tip that provides less resistance during intubation. These shaped tips also reduce the risk of internal injury. Thus, each bolus design facilitates the specific intubation procedure.

Another disadvantage of prior art boluses is their susceptibility to bending and kinking at a collar portion of the bolus that connects to a distal end of the enteral tube. Since the enteral tube is made of a material that is typically more flexible than the bolus, kinking readily occurs at the joint between the materials of differing flexibility. These boluses are also susceptible to bending at the fluid opening, where there is less material to provide rigidity to the bolus. This bending and kinking makes controlled intubation more difficult. Furthermore, the bending and kinking of the collar portion may also cause problems when using a wire stylet. The overall lengths of the stylet and tube are subject to certain assembly tolerances. When the length of the stylet is within the shorter dimension range and the length of the tube is within the longer dimension range, the stylet may not reach the collar portion of the bolus. If the bolus is bent near the collar portion, the stylet may pierce the tube. On the other hand, if the length of the stylet is within the longer dimension range and the length of the tube is within the shorter dimension range, the stylet may be positioned within the fluid opening. In this situation, the stylet may pass through the fluid opening if the bolus is bent or kinked.

It is therefore an object of the present invention to provide a bolus for an enteral feeding tube that provides delivery of fluid to a body cavity or aspiration of a body cavity that does not become occluded with mucous, gastrointestinal debris and coagulated feeding material.

It is also an object of the present invention to provide a bolus for an enteral feeding tube that approximates the fluid flow rate characteristics of an open-ended tube.

It is also an object of the present invention to provide a bolus for an enteral feeding tube that has an elongated collar portion and a fluid outlet that is biased toward the distal end of the bolus to allow for greater tolerances between the lengths of the stylet and tube while preventing a shorter length stylet from piercing the tube or a longer length stylet from passing through the fluid outlet if the bolus is bent or kinked.

It is also an object of the present invention to provide a single bolus that can be used in more than one intubation procedure, including an over-the-wire procedure, by providing a stylet passage at the bolus tip while maintaining a generally contoured tip to promote travel through tortuous anatomy.

These and other objects of the present invention will become readily apparent after review of the specification and accompanying drawings.

SUMMARY OF THE INVENTION

The present invention is a bolus for an enteral feeding tube, or catheter, that is capable of being used in an over-the-wire intubation procedure as well as other intubation procedures. The bolus has a generally tubular body defining a sidewall, a proximal end tube opening capable of being connected to a distal end of the enteral feeding tube, and a generally rounded terminal end having a flattened tip. The bolus includes a fluid opening within the sidewall of the bolus between the proximal end opening and the terminal end of the bolus. The fluid opening is biased toward the terminal end of the bolus thereby defining an elongated collar portion adjacent the proximal end tube opening of the bolus. The terminal end of the bolus has an aperture therethrough that forms a stylet passage in communication with the fluid opening. The stylet passage is sized to allow a stylet to pass therethrough when the tube is used in an over-the-wire intubation procedure.

The fluid opening includes a distal end and defines edge surfaces of the side wall of the bolus that converge and curve upwardly at the distal end of the opening near the terminal end of the bolus. Furthermore, an interior surface of the sidewall opposite the fluid opening is curved and slopes upwardly toward the distal end of the fluid opening. The curved interior surface and the fluid opening configuration allow for fluid flow that approximates the fluid flow rate characteristics of an open-ended tube.

DETAILED DESCRIPTION OF THE PREFERRED EMBODIMENTS

While the present invention will be described fully hereinafter with reference to the accompanying drawings, in which a particular embodiment is shown, it is to be understood at the outset that persons skilled in the art may modify the invention herein described while still achieving the desired result of this invention. Accordingly, the description which follows is to be understood as a broad informative disclosure directed to persons skilled in the appropriate arts and not as limitations of the present invention.

It should also be understood that while the description is made herein with reference to an enteral feeding tube, this description is by way of example only. The principles of the present invention may be applied to all types of catheter tubes, including Foley catheters, urethral catheters, and catheters for use in gastric, esophageal, pharyngeal, nasal, intestinal, rectalcolonic, choledochal, arterial, venous, cardiac and endobronchial applications.

Figure 1:
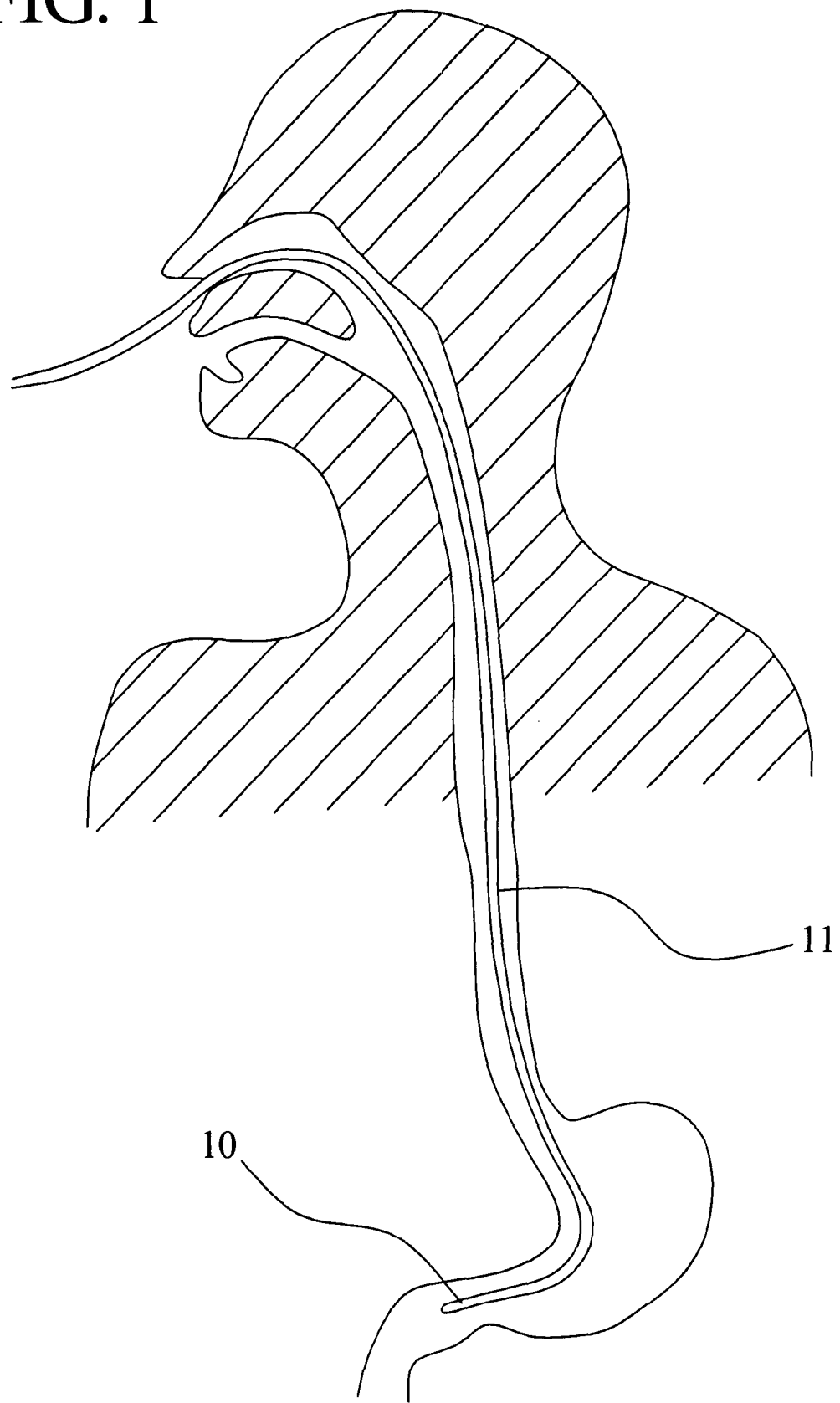
FIG. 1 is an illustration depicting an intubation configuration for an enteral feeding tube in a patient.
Figure 2:
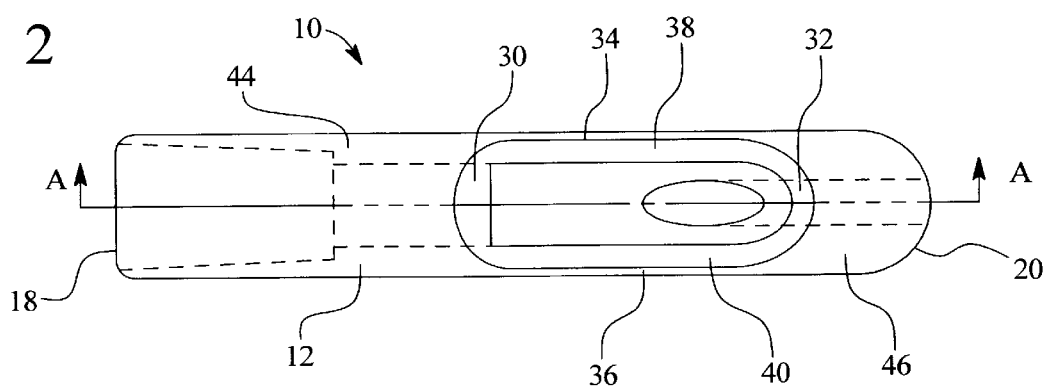
FIG. 2 is a plan view of a bolus of the present invention.
Figure 3:
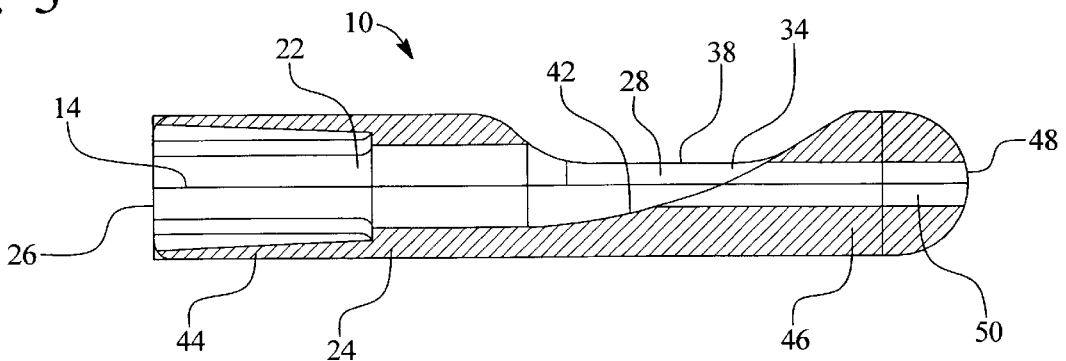
FIG. 3 is a cross-sectional view of the bolus depicted in FIG. 2 taken along section line A—A.

Referring to FIGS. 1–3, the present invention is a bolus 10 adapted to be connected to a distal end of an enteral feeding tube 11, as shown in FIG. 1. The bolus 10 can also be connected to the end of a catheter (not shown) for irrigation and aspiration of fluids within various body cavities of a patient. The bolus 10 has a generally tubular, or cylindrical, body 12 having a center axis 14. The body 12 includes a proximal end 18 and a distal, or terminal, end 20. The terminal end 20 is generally rounded and has a flattened tip configuration, as shown in FIGS. 2 and 3. The rounded configuration helps the bolus 10 to travel through tortuous anatomy, such as the gastrointestinal tract. The body 12 also includes a fluid passage 22 disposed within the body 12. The fluid passage 22 defines a bolus sidewall 24 and a proximal end tube opening 26. The tube opening 26 is adapted to be connected to, and in fluid communication with, a distal end of the enteral feeding tube 11, as shown in FIG. 1.

The fluid passage 22 diverges from the center axis 14 of the body 12 to define a fluid opening 28 through the sidewall 24, as shown in FIG. 3. The fluid opening 28 defines a proximal opening end 30, a distal opening end 32 and two generally vertical sidewalls 34 and 36 of the sidewall 24. The sidewalls 34 and 36 have edge surfaces 38 and 40, respectively. The edge surfaces 38 and 40 converge and curve upwardly at the distal end 32 of the opening 28. The edge surfaces 38 and 40 also curve upwardly adjacent to the proximal opening end 30, as shown in FIG. 3. An interior surface 42 of the sidewall 24 opposite the fluid opening 28 is curved and slopes upwardly toward the distal end 32 of the fluid opening 28. The interior surface 42 and the curved edge surfaces 38 and 40 of the fluid opening 28 allows for fluid flow that approximates the fluid flow rate characteristics of an open-ended tube.

The fluid opening 28 is biased toward the distal end 20 of the body 12, thereby defining an elongated collar portion 44 near the proximal end 18 of the body 12. The fluid opening also defines a distal end portion 46. The distal end 20 of the body 12 has an aperture 48 therethrough that forms a stylet passage 50 through the distal end portion 46 in communication with the fluid opening 28, as shown in FIG. 3. The stylet passage 50 is sized to allow a stylet (not shown) to pass therethrough when the tube is used in an over-the-wire intubation procedure. In a preferred embodiment, the stylet passage 50 has a diameter that is relatively smaller than a diameter of the fluid passage 28. Thus, the distal end portion 46 has a thicker material configuration than that of the sidewall 24 of the collar portion 44 of the body 12. The thick material provides rigidity to the distal end 20 of the body 12 and helps the bolus to travel through the gastrointestinal tract during the intubation procedure.

The overall lengths of a wire stylet (not shown) and tube (not shown) are subject to certain assembly tolerances. The elongated collar portion 44 and the forward-biased, or distal-biased, fluid opening 28 effectively allow for increased tolerances between the length of a wire stylet disposed within the enteral tube of an enteral tube/stylet assembly. The longer collar portion 44 creates a larger dimensional range in which a distal end of the wire stylet may be positioned while not falling short of the collar portion 44 or extending past the collar portion 44 and thereby residing within the fluid passage 22 at the fluid opening 28. The elongated collar portion 44 thereby prevents the stylet from piercing the tube adjacent to the collar portion 44 if the bolus is bent or kinked. The collar portion 44 also prevents the stylet from passing through the fluid opening 28 and potentially causing injury to the patient during intubation.

Figure 4:
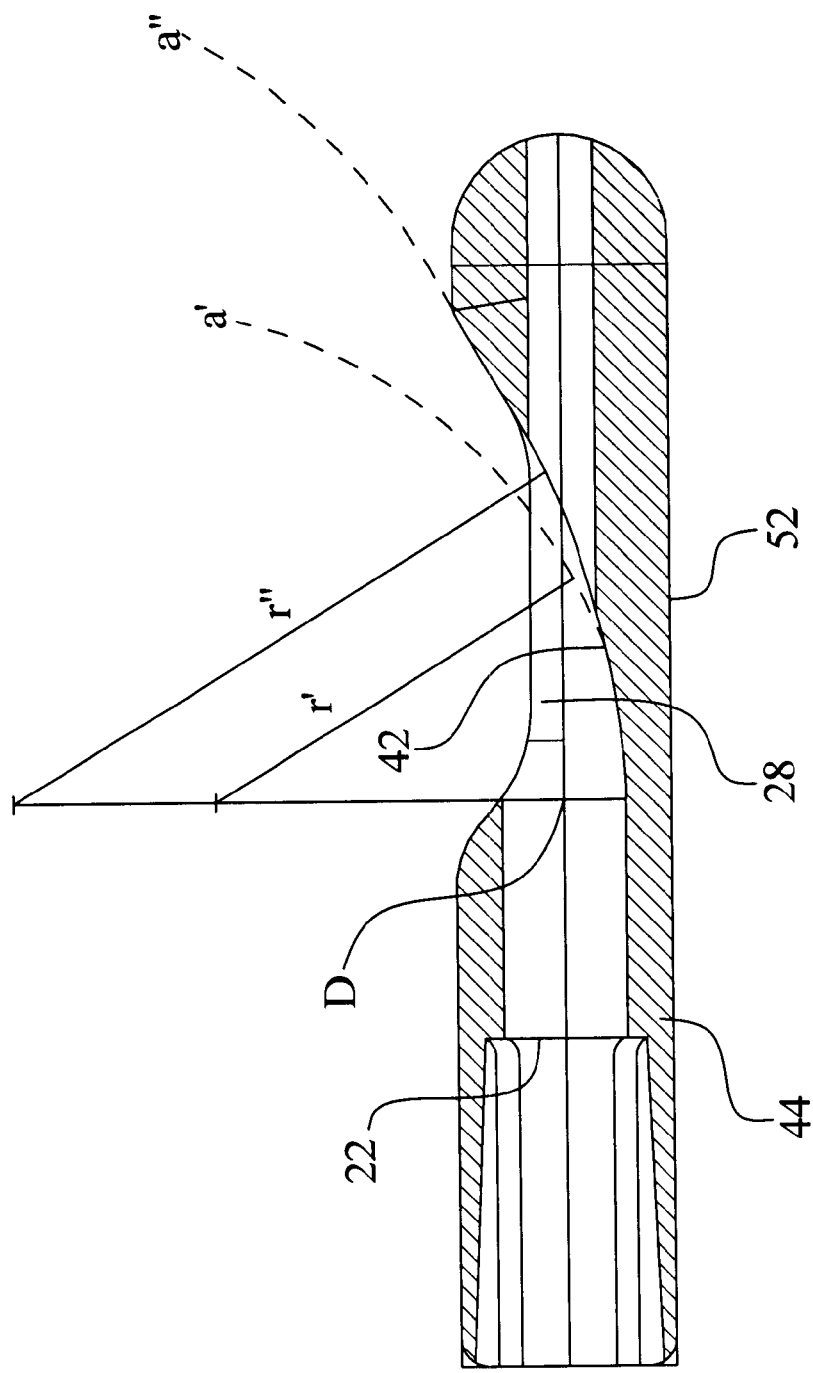
FIG. 4 is a cross-sectional view of the bolus depicted in FIG. 2 taken along section line A—A and depicting a range of curvatures of an interior surface of the bolus opposite a fluid opening.

The curved interior surface 42 is optimized to increase fluid flow through the fluid opening 28. FIG. 4 discloses a range of preferred curvatures of the curved interior surface 42. The curvature of the interior surface 36 is essentially a function of the inner diameter of the fluid passage 22 as characterized by a particular French size. The French size scale is most commonly used to describe the size of medical tubing such as enteral feeding tubing, urinary drainage tubing and catheters. The French scale (hereinafter "Fr.") is disclosed and compared against the American and English medical tubing size scales in Remington's Pharmaceutical Sciences (6th Ed. 1980; Mack Publishing Co.) pp. 1906–1907. Generally, the enteral feeding tubing employed in the present invention have French sizes from five to ten Fr. and are generally from 15 to 42 inches in length depending on whether the medical application is for neonatal, juvenile or adult patients.

The upward curvature of the interior surface 42 cannot be too severe otherwise obstruction of the fluid stream will result causing fluid turbulence and decreasing fluid flow output. On the other hand, the upward curvature of the interior surface 42 cannot be too shallow so as to require an overly long bolus to accommodate the more gradual incline.

FIG. 4 discloses curvatures for the interior surface 42 that maximize fluid flow rates. The selected range of curvatures is defined by arcs (a) circumscribed from radii (r) having lengths of between and including five times and ten times an inner diameter of the fluid passage 22 within the collar portion 44 and adjacent to the fluid opening 28, as indicated by the letter D in FIG. 4. In a preferred embodiment, the inner diameter D is equal to the inner diameter of the tubing. FIG. 4 generally discloses one end of the general range of preferred curvatures of the interior surface 42 in which an arc a' is circumscribed from a radius r' having a length equal to five times the inner diameter D. At the other end of the range of preferred curvatures, an arc a" is circumscribed from a radius r" having a length equal to ten times the inner diameter D.

In specific embodiments of the present invention, a six French enteral feeding tube having an inner diameter of about 0.055 inches requires the radius r defining the curvature of the interior surface 42 to have a length of about 0.489 inches or 8.890 times the inner diameter D. In an embodiment comprised of eight French enteral feeding tubing having an inner diameter of about 0.078 inches, the upward curvature of the interior surface 42 is defined by an arc circumscribed from a radius r having a length of 0.525 inches or 6.730 times the inner diameter D. In another specific embodiment of the present invention utilizing ten French enteral tubing having an inner diameter of 0.100 inches, the interior surface 42 was defined from an arc circumscribed from a radius having a length of 0.525 inches or 5.25 times the inner diameter D.

Another important feature of the present invention is the selective recessing or lowering of the height of the generally vertical side walls 34 and 36 defined by the fluid opening 28. A transverse sectional height is defined as the distance from an outside surface 52 of the sidewall 24 of the bolus 10 directly opposite the fluid opening to the edge surfaces 38 and 40. It has been found that the transverse sectional height of the vertical side walls 34 and 36 may range from a minimum height equal to one-half the inner diameter D. At a maximum, the transverse sectional height of the vertical side walls 34 and 36 should be no greater than the sum of the inner diameter D plus the thickness of the sidewall 24 of the bolus 10. The transverse sectional height may also be calculated in terms of the inner diameter of the tubing. In a preferred embodiment, the inner diameter D is equal to the inner diameter of the tubing. Therefore, in a preferred embodiment of the present invention, the transverse sectional height of the vertical side walls 34 and 36 is equal to about the inner diameter of the tubing.

If the transverse sectional height of the vertical side walls 34 and 36 is less than one half the inner diameter of the tubing, then bolus 10 has an increased tendency to kink or bend. On the other hand, if the vertical side walls 34 and 36 have a transverse sectional height greater than the sum of the inner diameter and thickness of the sidewall 22, this results in a vertical side wall height exceeding the outer configuration of bolus 10 thereby creating difficulty in intubation. Thus, the vertical side walls 34 and 36 are dimensioned to minimize kinking, bending, and occlusion of the fluid opening while maximizing fluid flow through the fluid opening.

The present invention provides a versatile bolus for an enteral feeding tube, or catheter, that is capable of being used in an over-the-wire intubation procedure in addition to other intubation procedures. The bolus provides a stylet passage in combination with a generally rounded distal end having a blunt tip. The stylet passage allows the bolus to be used for an over-the-wire intubation procedure and the blunt tip allows the bolus to be inserted in an intubation procedure while maintaining minimal resistance and minimizing occlusion of the fluid opening.

While the specific embodiments have been illustrated and described, numerous modifications come to mind without significantly departing from the spirit of the invention and the scope of protection is only limited by the scope of the accompanying Claims.

What is claimed is:

1. A bolus adapted for use with an enteral feeding tube, the bolus having a generally tubular body defining a sidewall, a proximal end tube opening capable of being connected to a distal end of the enteral feeding tube, and a generally rounded terminal end, the bolus including a fluid opening within the sidewall of the bolus between the proximal end opening and the terminal end of the bolus, the fluid opening biased toward the terminal end of the bolus, and an elongated collar portion adjacent the proximal end tube opening of the bolus, the collar portion defining and extending over a first passage within the bolus.

2. The bolus of claim 1, the fluid opening including a distal end and defining edge surfaces of the side wall of the bolus that converge and curve upwardly at the distal end of the fluid opening near the terminal end of the bolus.

3. The bolus of claim 1, wherein the bolus has an overall length and the elongated collar portion has a length that is at least one-third of the overall length of the bolus.

4. The bolus of claim 2, wherein the bolus has an overall length and wherein a distance from the proximal end tube opening of the bolus to a terminating point of the converged edge surfaces of the fluid opening is at least 90 percent of the overall length of the bolus.

5. The bolus of claim 2, wherein an interior surface of the sidewall opposite the fluid opening is curved and slopes upwardly toward the distal end of the fluid opening.

6. A bolus adapted for use with an enteral feeding tube, the bolus having a generally tubular body defining a sidewall, a proximal end tube opening capable of being connected to a distal end of the enteral feeding tube, and a generally rounded, non-conical terminal end, the bolus including a fluid opening within the sidewall of the bolus between the proximal end opening and the terminal end of the bolus, the fluid opening biased toward the terminal end of the bolus, and an elongated collar portion adjacent the proximal end tube opening of the bolus, the collar portion defining and extending over a first passage within the bolus, the terminal end of the bolus having an aperture therethrough and forming a stylet passage in communication with the fluid opening, the stylet passage sized to allow a stylet to pass therethrough when the tube is used in an over-the-wire intubation procedure.

7. The bolus of claim 6, the fluid opening including a distal end and defining edge surfaces of the side wall of the bolus that converge and curve upwardly at the distal end of the fluid opening near the terminal end of the bolus.

8. The bolus of claim 6, wherein the bolus has an overall length and the elongated collar portion has a length that is at least one-third of the overall length of the bolus.

9. The bolus of claim 7, wherein the bolus has an overall length and wherein a distance from the proximal end tube opening of the bolus to a terminating point of the converged edge surfaces of the fluid opening is at least 90 percent of the overall length of the bolus.

10. The bolus of claim 6, wherein the aperture through the terminal end of the bolus defines a generally tubular second passage through the terminal end of the bolus.

11. The bolus of claim 10, wherein the first passage has a diameter and the second passage has a diameter that is less than the diameter of the first passage, thereby defining a thicker sidewall within the terminal end of the bolus than the sidewall within the collar portion of the bolus.

12. The bolus of claim 11, wherein an interior surface of the sidewall opposite the fluid opening is curved and slopes upwardly toward the distal end of the fluid opening.

13. The bolus of claim 12, wherein the second passage passes through the curved interior surface of the sidewall.

14. A bolus adapted for use with an enteral feeding tube capable of being used in an over-the-wire intubation procedure, the bolus comprising:
a generally cylindrical body having a center axis and a proximal end including an end opening capable of being connected to a distal end of the enteral feeding tube, the opening in fluid communication with a fluid passage disposed within the body and along its center axis thereby defining a cylindrical sidewall, the fluid passage diverging from the center axis of the body and exiting through the sidewall to define a fluid outlet and a curved fluid passage surface, the fluid outlet defining an elongated collar portion and a distal end portion of the body, the collar portion defining and extending over a first passage within the bolus, the distal end portion including a generally rounded, non-conical terminal end;
the fluid outlet including a distal end and further defining edge surfaces of the side wall of the body having planar and distal curved portions, the distal curved portions converging and curving upwardly at the distal end of the outlet to form a curved outlet surface, the curved outlet surface terminating at a point immediately adjacent the generally rounded terminal end of the distal end portion of the body;
the distal end portion of the body including a stylet passage disposed along the center axis of the body that passes through the non-conical terminal end of the distal end portion and the curved fluid passage surface of the fluid passage, the stylet passage sized to allow a stylet to pass therethrough when the tube is used in an over-the-wire intubation procedure.

15. The bolus of claim 14, wherein the body of the bolus has an overall length and wherein a distance from the proximal end of the body to the terminating point of the curved outlet surface is at least 90 percent of the overall length of the body of the bolus.

16. The bolus of claim 14, wherein the planar edge surfaces of the sidewall defined by the fluid outlet are offset from a plane parallel to the planar edge surfaces and passing through the center axis of the body in a direction generally outwardly from the curved outlet surface.

17. The bolus of claim 14, wherein the fluid passage has a diameter and the stylet passage has a diameter that is less than the diameter of the fluid passage, thereby defining a thicker sidewall within the distal end of the body of the bolus than the sidewall within the collar portion of the body of the bolus.

18. The bolus of claim 17, wherein the curved fluid passage surface is defined by an arc circumscribed from a radius having a length equal to at least five times the diameter of the fluid passage.

19. An enteral feeding tube for administration and aspiration of fluids within the gastrointestinal tract, the tube having a wall of selected thickness, a proximal end of the tube capable of being connected to a fluid nutrient source, a distal end of the tube comprising:
a bolus having a proximal end in fluid communication with the tube, a fluid passage in fluid communication with the proximal end and having a diameter and defining a bolus sidewall, a generally rounded, non-conical terminal end, and a fluid opening in the sidewall of the bolus, the fluid opening in fluid communication with the passage, the fluid opening biased toward the terminal end of the bolus, and an elongated collar portion adjacent the proximal end of the bolus, the collar portion defining and extending over a first passage within the bolus, the terminal end of the bolus having an aperture therethrough and forming a stylet passage in communication with the fluid passage, the stylet passage sized to allow a stylet to pass therethrough when the tube is used in an over-the-wire intubation procedure.

20. The enteral feeding tube of claim 19, wherein the bolus is more rigid than the tube.

21. The enteral feeding tube of claim 19, the fluid opening including a distal end and defining edge surfaces of the side wall of the bolus that converge and curve upwardly at the distal end of the outlet near the terminal end of the bolus.

22. The enteral feeding tube of claim 21, wherein an interior surface of the sidewall opposite the fluid opening is curved and slopes upwardly toward the distal end of the fluid opening.

23. The enteral feeding tube of claim 22, wherein the stylet passage passes through the curved interior surface of the sidewall.

24. The enteral feeding tube of claim 22, wherein the curved interior surface is defined by an arc circumscribed from a radius having a length that is approximately 5.25 times the diameter of the fluid passage for a 10 French tube size.

25. The enteral feeding tube of claim 22, wherein the curved interior surface is defined by an arc circumscribed from a radius having a length that is approximately 6.7 times the diameter of the fluid passage for an 8 French tube size.

26. The enteral feeding tube of claim 22, wherein the curved interior surface is defined by an arc circumscribed from a radius having a length that is approximately 8.9 times the diameter of the fluid passage for a 6 French tube size.

27. A catheter for irrigation and aspiration of fluids within body cavities, the catheter including a catheter tube having a wall of selected thickness and a proximal end capable of being connected to one of a fluid and suction source, a distal end of the catheter tube comprising:
a bolus having a proximal end in fluid communication with the catheter, a fluid passage in fluid communication with the proximal end and defining a bolus sidewall, a generally rounded, non-conical terminal end, and a fluid opening in the sidewall of the bolus, the fluid opening in fluid communication with the passage, the fluid opening biased toward the terminal end of the bolus, and an elongated collar portion adjacent the proximal end of the bolus, the collar portion defining and extending over a first passage within the bolus, the terminal end of the bolus having an aperture therethrough and forming a stylet passage in communication with the fluid passage, the stylet passage sized to allow a stylet to pass therethrough when the catheter is used in an over-the-wire intubation procedure.

28. The catheter of claim 27, wherein the bolus is more rigid than the catheter tube.

29. The catheter of claim 27, the fluid opening including a distal end and defining edge surfaces of the side wall of the bolus that converge and curve upwardly at the distal end of the outlet near the terminal end of the bolus.

30. The enteral feeding tube of claim 29, wherein an interior surface of the sidewall opposite the fluid opening is curved and slopes upwardly toward the distal end of the fluid opening.

31. The enteral feeding tube of claim 30, wherein the stylet passage passes through the curved interior surface of the sidewall.

32. The enteral feeding tube of claim 30, wherein the curved interior surface is defined by an arc circumscribed from a radius having a length that is approximately 5.25 times the diameter of the fluid passage for a 10 French tube size.

33. The enteral feeding tube of claim 30, wherein the curved interior surface is defined by an arc circumscribed from a radius having a length that is approximately 6.7 times the diameter of the fluid passage for an 8 French tube size.

34. The enteral feeding tube of claim 30, wherein the curved interior surface is defined by an arc circumscribed from a radius having a length that is approximately 8.9 times the diameter of the fluid passage for a 6 French tube size.

\* \* \* \* \*